(12) United States Patent
Dehal et al.

(10) Patent No.: US 8,669,110 B2
(45) Date of Patent: Mar. 11, 2014

(54) USES OF REAGENTS IN SAMPLE COLLECTION AND CARTRIDGE SYSTEMS

(76) Inventors: Prabhjyot Dehal, Dundee (GB); David Pritchard, Dundee (GB); Claire Geekie, Dundee (GB)

( * ) Notice: Subject to any disclaimer, the term of this patent is extended or adjusted under 35 U.S.C. 154(b) by 534 days.

(21) Appl. No.: 12/933,670

(22) PCT Filed: Mar. 20, 2009

(86) PCT No.: PCT/EP2009/053327
§ 371 (c)(1),
(2), (4) Date: Nov. 22, 2010

(87) PCT Pub. No.: WO2009/115608
PCT Pub. Date: Sep. 24, 2009

(65) Prior Publication Data
US 2011/0059547 A1    Mar. 10, 2011

(30) Foreign Application Priority Data
Mar. 20, 2008 (GB) .................................. 0805296.1

(51) Int. Cl.
*G01N 33/48* (2006.01)
(52) U.S. Cl.
USPC ............... 436/17; 436/8; 436/174; 422/430; 422/68.1
(58) Field of Classification Search
USPC ............ 422/400, 401, 405, 419, 430, 68.1; 436/8, 17, 174
See application file for complete search history.

(56) References Cited

U.S. PATENT DOCUMENTS

| | | | |
|---|---|---|---|
| 3,862,302 A * | 1/1975 | Price et al. ................. | 436/521 |
| 3,988,429 A * | 10/1976 | Richards et al. ............ | 424/1.17 |
| 4,891,319 A | 1/1990 | Roser | |
| 5,482,719 A * | 1/1996 | Guillet et al. ............... | 424/486 |
| 5,565,318 A | 10/1996 | Walker et al. | |
| 5,624,597 A | 4/1997 | Buhl et al. | |
| 5,776,563 A * | 7/1998 | Buhl et al. ................... | 428/34.1 |
| 2004/0137417 A1 | 7/2004 | Ryan | |

FOREIGN PATENT DOCUMENTS

| | | |
|---|---|---|
| EP | 0419168 A2 | 3/1991 |
| GB | 2446309 A | 8/2008 |
| JP | 63015161 A | 1/1988 |
| WO | 9944066 A1 | 9/1999 |
| WO | 2004073864 A2 | 9/2004 |
| WO | 2008020013 A2 | 2/2008 |

OTHER PUBLICATIONS

Viskanic, Martino, International Search Report, PCT/EP2009/053327, European Patent Office, Oct. 16, 2009.
Wood, Richard, Great Britain Search Report, Date of Search: Dec. 2, 2008, Great Britain Application Number: GB0805296.1.

* cited by examiner

*Primary Examiner* — Christopher A Hixson
(74) *Attorney, Agent, or Firm* — Ober, Kaler, Grimes & Shriver; Royal W. Craig

(57) ABSTRACT

Provided is a sample collection container comprising one or more reagent bodies, wherein each body comprises one or more reagents confined by a restraining agent, wherein the restraining agent is capable of being broken down to release the one or more reagents, and wherein the one or more reagents are dispersed through the restraining agent.
Further provided is a cartridge system comprising:
(a) a reagent component for storing one or more reagents; and
(b) a processing component for processing the one or more reagents in an assay;
wherein one or more of the components comprise one or more reagent bodies, wherein each body comprises one or more reagents confined by a restraining agent, wherein the restraining agent is capable of being broken down to release the one or more reagents, and wherein the one or more reagents are dispersed through the restraining agent; and further wherein the reagent component and the processing component are configured to be coupled together to form a cartridge, and wherein the reagent component and/or the processing component comprise at least one compartment configured to accept waste from the assay, the reagent component not taking part in processing the reagents in the assay, except to accept waste from the processing component.

42 Claims, 7 Drawing Sheets

Figure 1A:
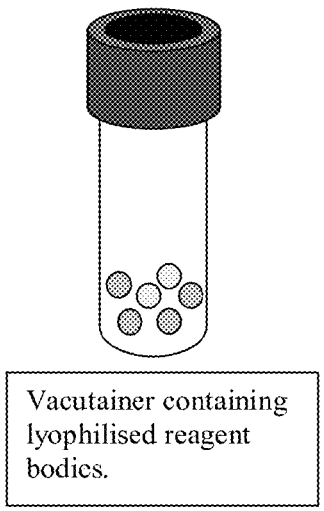

Vacutainer containing lyophilised reagent bodies.

Vacutainer containing lyophilised reagent bodies.

Lyophilised restraining agent and reagents dissolve after addition of sample, thereby starting incubation period before sample is introduced to an analyser.

USES OF REAGENTS IN SAMPLE COLLECTION AND CARTRIDGE SYSTEMS

CROSS REFERENCE TO RELATED APPLICATIONS

This application is a U.S. National Stage Application filed under 35 U.S.C. §371 and claims priority to International Application No. PCT/EP09/53327, filed Mar. 20, 2009, which application claims priority to Great Britain Application No. 0805296.1, filed on Mar. 20, 2008, the disclosure of which are incorporated herein by reference.

The present invention concerns a sample collection container comprising one or more reagents which are confined by a restraining agent. On addition of a sample to the container, the reagents are released into the sample. The present invention also concerns methods for collecting and processing samples and uses of the sample collection container.

The present invention also concerns a cartridge system for use in detecting one or more analytes in a sample, especially a biological sample. The system is typically a two-component system, and comprises a reagent component and a processing component. The reagents are confined during storage in the reagent component and released, for example, when contacted with a fluid. The cartridge system may comprise a sample collection zone suitable for receiving the sample collection container according to the present invention. The present invention also concerns an assay method and uses relating to the cartridge system.

Sample collection devices and storage containers have advanced recently to allow easy, quick and safe means to collect samples, particularly biological samples from a patient. The Vacutainer™ (produced by Becton, Dickinson and Company) is an advanced test tube which contains a rubber cap. The Vacutainer™ is used to collect blood samples. When the rubber cap is pierced a vacuum in the tube causes blood to pass from the needle in the patient into the tube. Vacutainers™ may include one or more stabilisation or separation additives, such as anticoagulant or clot activator and a gel for serum separation, which mix with the blood when collected. Anticoagulants or clot activator allow a clot to form, which may then be ready for later down stream analysis.

WO2007/076023 discloses assay modules comprising reagents either in free form or supported on solid phases including the surfaces of the compartments in the assay modules.

Despite the advancement made to date in sample collection containers, particularly the Vacutainer™, there is an ongoing requirement for more simplified and rapid analysis techniques for samples and also an ongoing requirement to increase the shelf life of reagents for such analysis techniques.

It is an aim of the present invention to solve the above problems and improve on known products and methods, such as those outlined above.

Accordingly, in the first aspect of the present invention a sample collection container comprising one or more reagent bodies, wherein each body comprises one or more reagents confined by a restraining agent, wherein the restraining agent is capable of being broken down to release the one or more reagents, and wherein the one or more reagents are dispersed through the restraining agent.

In the reagent bodies the reagents are prevented from reacting and/or stabilized by the restraining agent before the sample is added. When the sample is taken, for example blood is drawn from a patient through a needle and into the sample collection contain, the bodies mix with the sample and the restraining agent of each body is broken down to release the one or more reagents. This is particularly advantageous because it allows immediate incubation of the sample with one or more reagents required for sample processing and/or analysis and, therefore, reduces the incubation time required in the later stages of processing and analysis. Therefore, methods of analysis of samples are faster when the collection containers according to the present invention are used. Many protocols require short sample-to-result timeframes. The sample collection containers according to the present invention will be very beneficial for such protocols.

The reagents may have a longer shelf life in the sample collection containers because the restraining agent of the may act to stabilise the reagents. This may be particularly advantageous for reagents which previously required storage at low temperatures or had a short shelf life.

Methods of stabilizing reagents, particularly biological reagents, are known in the art. For example, U.S. Pat. Nos. 5,763,157 and 5,565,318 disclose a reagent semi-sphere comprising at least one biological reagent and a glass forming filler material, wherein the reagent semi-sphere is room temperature stable, water soluble and has a $T_g$ above room temperature. U.S. Pat. No. 5,763,157 discloses that at least two carbohydrates are combined to create the reagent sphere. The use of carbohydrates to stabilize antibodies, gene delivery systems and DNA restriction and modifying enzymes in freeze-dried formulations has also been investigated (Andya J. D. et al.; "Mechanism of Aggregate Formation and Carbohydrate Excipient Stabilization of Lyophilized Humanized Monoclonal Antibody Formulations"; AAPS PharmSci 2003; 5 (2) Article 10), (Talsma H. et al., "Stabilization of gene delivery systems by freeze-drying"; International Journal of Pharmaceutics, Volume 157, Issue 2, 28 Nov. 1997, pages 233-238) and (Calaco C. et al., "Extraordinary Stability of Enzymes dried in Trehalose: Simplified Molecular Biology"; Bio/Technology 10, pages 1007-1011 (1992))

The reagent bodies used in the present invention each comprise one or more reagents confined by a restraining agent.

The term "reagent body" in the context of the present invention means that the one or more reagents and restraining agent form separate entities or individual units. The bodies may be in any suitable form such as, for example, a bead, a capsule or a pearl. The bodies may be in any suitable shape, for example a sphere or semi-sphere, wherein the sphere or semi-sphere may have a uniform or non-uniform outer surface. The dimensions and volume of the bodies is not particularly limited and the volume may be in the range of 1 to 500 microliters, preferably 10 to 50.

The bodies are advantageous because they may allow desired quantities of reagents to be added to sample collection containers easily. The bodies may also be easily introduced into the sample collection container.

In one embodiment, the one or more reagents are confined (encapsulated) by an outer shell surrounding one or more reagents, wherein the outer shell comprises the restraining agent. In this embodiment, the reagent bodies may be in the form of a capsule, wherein the one or more reagents are confined (encapsulated) in the core of the capsule and the restraining agent forms an outer shell which encapsulates/envelopes/surrounds the core of reagents—in this embodiment, the outer shell may also have the reagents dispersed within it, and may therefore act as an encapsulating shell as well as a medium for holding the reagents.

In a particularly preferred embodiment, the one or more reagents are confined in a mixture with the restraining agent. This typically involves the one or more reagents being dispersed or distributed throughout a matrix of surrounding restraining agent. This dispersion or distribution may be uniform or non-uniform and may be a course or a fine dispersion. Thus the dispersion may comprise aggregates of the reagent or individual molecules of the reagent distributed within the restraining agent. Thus, each body may be a uniform/consistent or non-uniform/non-consistent composition of the one or more reagents and the restraining agent.

The term "confined by a restraining agent" in the context of the present invention means that the restraining agent in each body acts to confine/restrain/restrict the one or more reagents in the form of the reagent bodies. The restraining agent acts to prevent the one or more reactants reacting and/or stabilise the one or more reactants. The restraining agent may achieve this by, for example, reversibly reacting with the one or more reagents or by physically separating, sequestering or confining the reagents from each other and the surrounding environment, other reactants and the like. The restraining agent may act, for example, as a sequestration agent by sequestering the one or more reagents in the manner of EDTA acting to sequester metal ions or the like.

The restraining agent may act to stabilise the one or more reagents and/or prevent the reagents from mixing/reacting and/or prevent the reagents from being oxidised. The reagents may therefore, have extended shelf life and/or be able to withstand high temperatures allowing them to be stored, for example at room temperature.

In the embodiment wherein the one or more reagents are confined by an outer shell surrounding one or more reagents, the restraining agent forms the outer shell around a core of the reagents. The use of an outer shell is particularly advantageous to stabilise the one or more reagents and/or prevent the reagents from mixing/reacting and/or prevent the reagents from being oxidised.

In the embodiment wherein the one or more reagents are confined in a mixture with the restraining agent, the restraining agent may act as a matrix or medium wherein the one or more reactants are uniformly or non-uniformly dispersed or spread throughout.

In a further embodiment, the one or more reagents may be confined in a mixture with the restraining agent and confined by an outer shell formed from the restraining agent, as discussed above.

The restraining agent may be formed of any suitable substance, which preferably has very little or no biochemical or biophysical effect on the activity of one or more reagents and any reaction which takes place between the one or more reagents and the sample.

The restraining agent is formed of a material which can be broken down sufficiently to release the one or more reagents from the body. In the embodiment wherein the body has an outer shell, the outer shell is broken down to release the one or more reagents from the core of the body. In the embodiment wherein the restraining agent is mixed with the one or more reagents, the restraining agent is broken down in the mixture to release the one or more reagents.

The term "broken down" in the context of the present invention is not especially limited and means that the restraining agent may be broken down by any means to release the one or more reagents. Typically the restraining agent is either completely or partially disintegrated to allow release of the one or more reagents. For example, the restraining agent may be broken down by being sublimed, melted, liquefied, dissolved, decayed, decomposed or the like. Preferably, the restraining agent is capable of being broken down when contacted with a fluid. The fluid may break down the restraining agent by decaying the restraining agent. The restraining agent may be broken down typically by enzymatic degradation of the restraining agent or bacterial decomposition of the restraining agent.

The restraining agent may be broken down chemically by dissolving in a liquid such as water. The sample may preferably be used as the liquid to dissolve the outer shells, thus releasing the reagents into the sample on contact and allowing immediate incubation with the reagents.

In this embodiment, the restraining agent is preferably formed from a dried substance which dissolves when contacted with the sample. In this embodiment, the one or more reagents are also in dried form with the restraining agent. The restraining agent and the one or more reagents may be desiccated or lyophilised.

The restraining agent preferably comprises one or more carbohydrates. Any suitable carbohydrates may be used, for example sucrose and trehalose. In this embodiment, wherein the restraining agent comprises one or more carbohydrates, the restraining agent and the reagents are preferably desiccated or lyophilised.

Capsules which release confined reagents in a in a specific manner are well known in the pharmaceutical industry. For example, the article Singh B. "Modified-Release Solid Formulations for Colonic Delivery" Recent Patents on Drug Delivery & Formulations 2007, 1, 53-63, discloses solid formulations for targeted drug release into the lower GI tract allowing a single or combination of two or more physiological characteristics of the colon to control drug release. The reagents are enveloped in a polymer of varying composition (to dissolve at different pH levels or in different solutions, e.g. detergents) or thickness (to dissolve more slowly). These capsules may be used in the present invention.

Accordingly, in the embodiment wherein the one or more reagents are confined by an outer shell surrounding one or more reagents, the outer shell may be broken down to release the one or more reagents at a given pH, after a certain length of time and/or when contacted with a specific solution. This is particularly advantageous for reagents which are liquid unstable, and therefore unsuitable for pre-mixing.

In this embodiment, the restraining agent in the outer shell comprises one or more substances which are suitable for controlled break down. For example, the controlled break down may be caused by a specific pH or contact with a specific sample solution. The thickness of outer shell may be set to a suitable thickness in order to control how quickly the outer shell is broken down and, therefore, the time of release of the one or more reagents. The restraining agent may comprise, for example, any suitable polymer which is known to be suitable for coating capsules. Commonly used polymers include derivatives of acrylic acid and cellulose. The restraining agent may be broken down by any suitable means, such as detergents, light sensitive bonds, enzymatic degradation and the like. In the embodiment, wherein the restraining agent comprises light sensitive bonds, the bonds may be sensitive to light having any suitable wavelength but is preferably visible light having a wavelength of 360 to 720 nm. The restraining agent may be broken down when contacted with the sample, such as whole blood, which provides a natural co-factor or enzyme which acts to break down the restraining agent in the outer shell.

In the embodiment wherein the one or more reagents are confined in a mixture with the restraining agent, the restraining agent may also comprise one or more substances which are suitable for controlled break down by for example pH, e.g.

when in contact with a specific solution. The amount of restraining agent in the mixture may be set to a suitable amount in order to control how quickly the restraining agent is broken down and, therefore, the time of release of the one or more reagents. As above, the restraining agent may comprise a suitable polymer such as derivatives of acrylic acid and cellulose.

Figure 4:
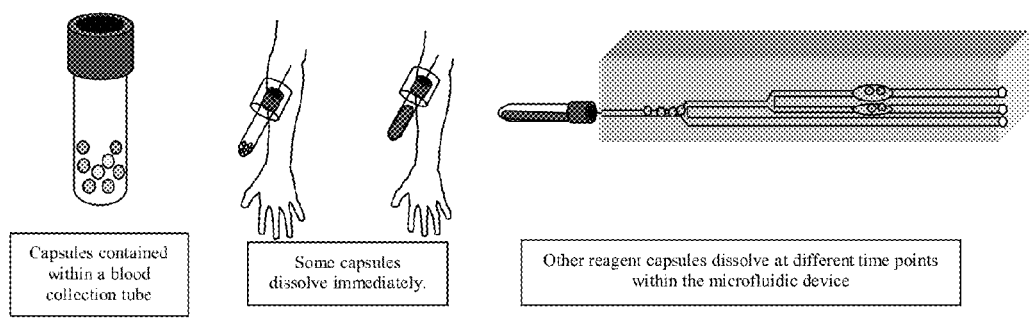

The sample collection container may comprise two or more different types of reagent bodies, wherein the restraining agents differ in order to allow release of different reagents at different time periods and/or different pHs and/or when contacted with different solutions. This is particularly advantageous because it allows for example, some reagents to be released when the sample is collected in the sample collection container and other reagents to be released from the bodies during downstream analysis steps. This is shown in FIG. 4, wherein some reagents are released when the blood is collected in the collection tube and other reagents are released later in the microfluidic device. This allows a faster time to result for assays, simplifies the analytical process and reduces cost.

The bodies may be manufactured using techniques well known to a person skilled in the art. An example protocol of how the reagent bodies according to the present invention may be produced is provided in Example 1.

The sample collection container according to the present invention is preferably suitable for collection of biological samples selected from blood, saliva, urine, amniotic fluid, mucus, ascites fluid, pulmonary liquids (including pleural), lavage (for example pulmonary eastric etc.), biopsy fluid, semen, swabs (for example PAP, oral etc.), sweat, tears, faecal stools, cerebrospinal fluid, wound exudate, synovial fluid and the like. In a preferred embodiment the sample collection container is a Vacutainer™ comprising the reagent bodies, as defined above. Typically, the sample collection container according to the present invention does not include assay modules including assay plates, cartridges, multi-well assay plates, reaction vessels and the like.

Figure 1B:
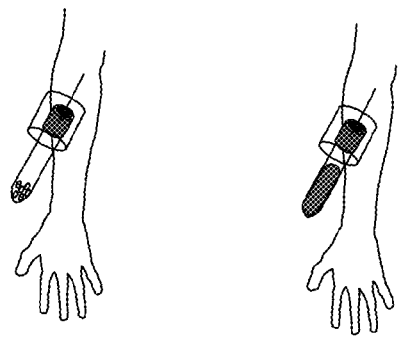
Figure 1C:
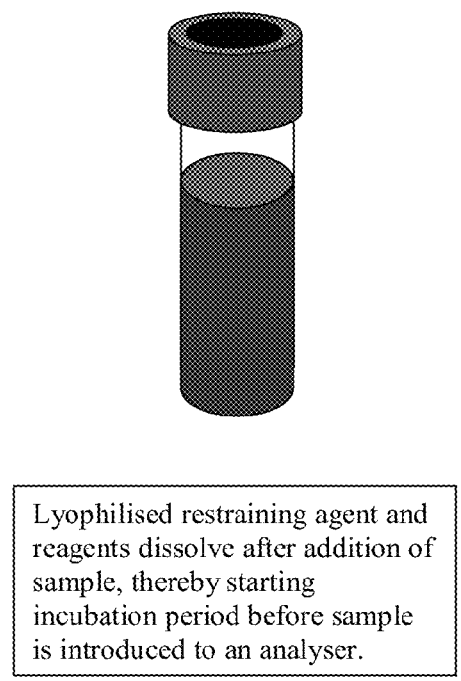

FIG. 1 shows a sample collection container according to the present invention; in FIG. 1a a Vacutainer™ comprising lyophilised reagent bodies is shown during its storage state; in FIG. 1b the a Vacutainer™ is being used to withdraw a sample of blood from a patient; in FIG. 1c a Vacutainer™ is shown after the sample has been collected and the sample has contacted with the bodies and dissolved the restraining agent to release the reagents into the sample and start incubation before the sample is introduced into an analyser.

Figure 2A:
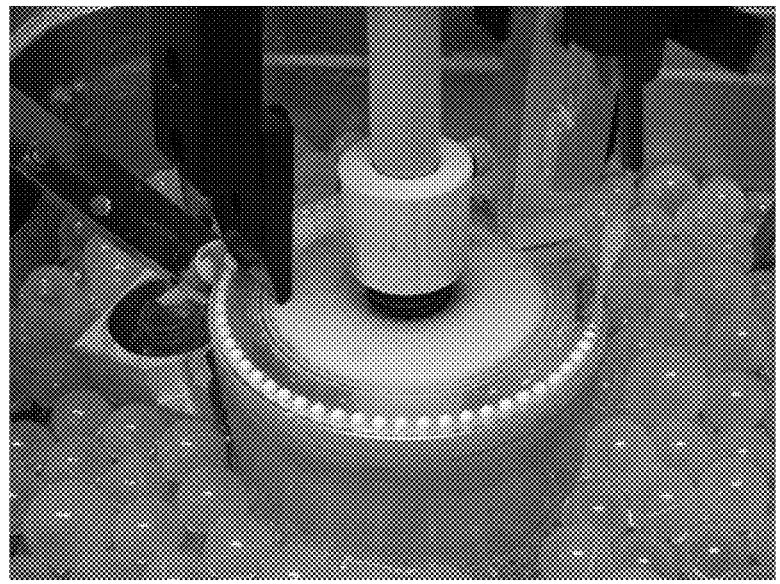
Figure 2B:
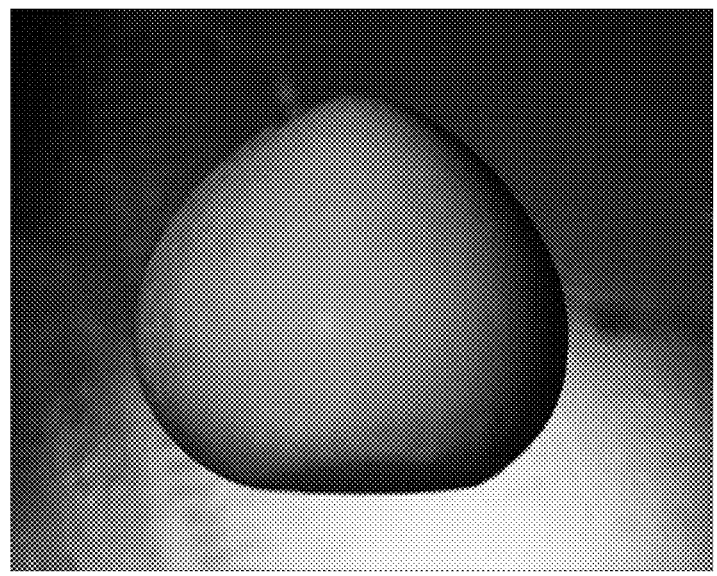

FIG. 2a shows a stage in the manufacture of reagent bodies and FIG. 2b shows a manufactured reagent body by Axis Shield which may be used in the present invention.

The one or more reagents in the bodies may be any suitable reagent required to process and/or analyse a sample. For example, the one or more reagents are suitable for carrying out one or more processing steps selected from analyte and/or sample preparation, analyte and/or sample separation, analyte and/or sample concentration, analyte and/or sample amplification, an analyte and/or sample purification, an analyte and/or sample labelling, and an analyte and/or sample detection.

In one embodiment the sample collection container comprises two or more reagents, wherein the two or more reagents are encapsulated in the one or more bodies. In this embodiment the two or more reagents may be encapsulated together in the same body, or separately in two or more different bodies. The sample collection container may also comprise a mixture of bodies comprising two or more different reagents and bodies comprising one type of reagent.

The one or more reagents are preferably independently selected from a protein, a polypeptide, a peptidomimetic, a nucleic acid, an oligonucleotide, an aptamer and organic or inorganic chemical reagents. Preferably the one or more reagents are independently selected from an antibody or a fragment of an antibody, a receptor or a fragment of a receptor, an antigen, an enzyme, an enzyme inhibitor, a binding protein, a catalyst, a blood clotting activator, an anticoagulant, a serum separating agent a detergent and a salt.

The reagents are preferably for enzymatic assays, RNA assays, protein assays or ALT enzymatic assays. Examples of preferred reagents include protease inhibitors, RNAse inhibitors, RNAase, reverse transcriptase, DNA polymerase, SYBR green, =concanavalin A, magnetic antibodies, magnetic microparticles and magnetic nanoparticles such as MACS® beads (Miltenyi Biotech™), guanidine isothiocyanate, glycogen, RNA carrier, sodium chloride, dNTPs, magnesium chloride, and bridging agents such as StemSep®.

The sample collection container may also comprise one or more reagents which are not confined in the bodies. The non-confined reagents are preferably desiccated or lyophilised. Any of the above defined reagents may be present in the container and not confined in the bodies. Particularly preferred reagents which are not confined are blood clotting activator, an anticoagulant, a detergent and a salt.

In one embodiment the one or more reagents are labels for one or more analytes. The analyte preferably comprises a virus or virus particle or virus component, a protein, a polypeptide, a glycoprotein, a nucleic acid, such as DNA or RNA, an oligonucleotide, a metabolite, a carbohydrate such as a complex carbohydrate, a lipid, a fat, or an endogeneous or exogeneous small molecule such as a pharmaceutical or drug.

In one embodiment the one or more reagents are magnetic or magnetisable and/or are attached to a magnetic or magnetisable substance. In this embodiment the one or more reagents may be magnetic beads or the one or more reagents are attached to magnetic beads. Alternatively the one or more reagents may be magnetic proteins or the one or more reagents are attached to magnetic proteins. In one embodiment, the reagent may be a magnetic liposome.

This embodiment provides a further advantage because it allows a magnetic field to be used on the sample collection container to influence the one or more reagents. The magnetic field may be used, for example, to mix the one or more reagents with the sample. The speed of mixing the reagents and the sample may be aided by the use of a reversible magnetic field.

In a preferred embodiment, when the one or more reagents are magnetic or magnetisable and/or are each attached to a magnetic or magnetisable substance, each of the one or more reagents comprise a label for analyte. One or more different types of labels for different analytes may be present in the sample collection container. Each reagent may comprise one or more of the same or different types of labels.

When the sample is added to the sample collection container, the one or more reagents are released allowing the label to attach to any analyte present in the sample. A magnetic field may then be used to separate, purify and/or isolate the labels and/or analytes that may be attached to the labels, from one or more further substances in the sample. This is particularly advantageous because it allows separation/purification/isolation of analytes on a macroscale ready for analysis on a microscale or nanoscale. A large proportion of the sample may then be disposed of at a macroscale level. Therefore, this embodiment allows significantly larger starting volumes of the initial sample, such as blood, saliva or urine, to be concentrated into smaller volumes used in further downstream analysis while retaining as much of the original analyte as possible from the initial sample. It also further helps to speed up the whole process of sample analysis due to the rapid separation/purification/isolation of the analyte. This embodiment also allows disposal of undesired substances from the sample in the collection container and thus reduces exposure to such substances. This is particularly advantageous when hazardous substances are present in the sample, especially blood, for which it is desirable to keep operator exposure to a minimum.

Figure 3:
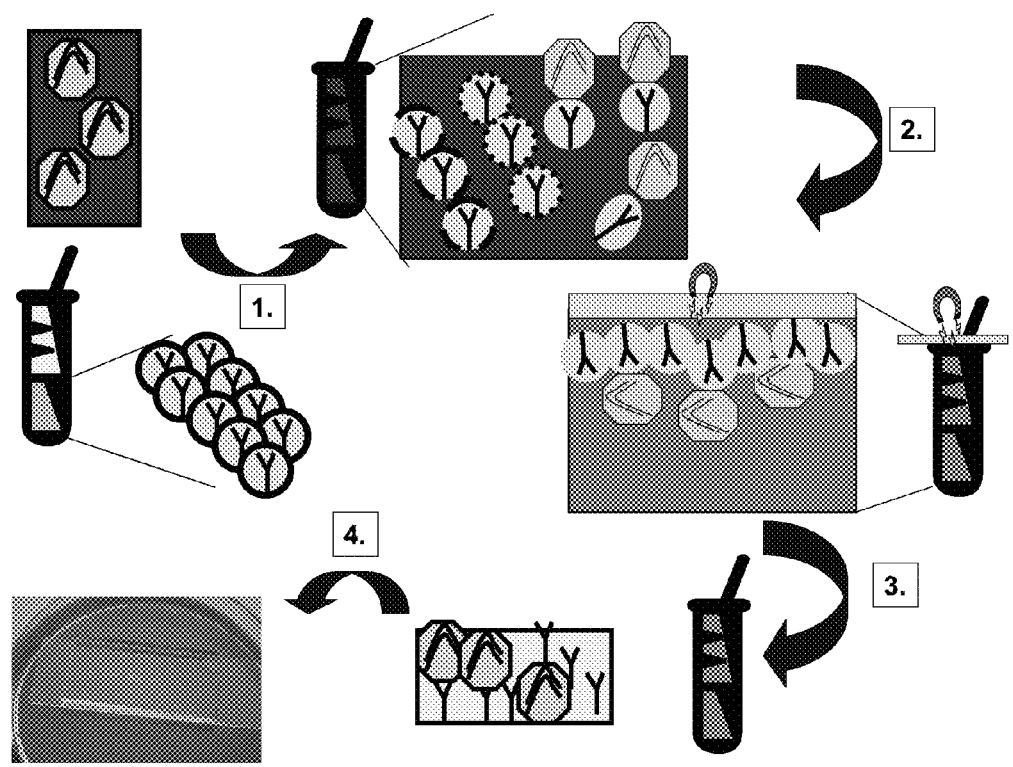

FIG. 3 shows a method of sample collection and processing employing the sample collection tubes according to the present invention. In step 1 blood is introduced into the sample collection tube comprising the reagent bodies, wherein the reagents include a magnetic particle or protein (Y); the sample and the reagents mix which leads to breakdown of bodies and release of the magnetic particles or proteins, some of which bind to the target analyte in the sample; in step 2 a magnetic force is applied to the tube and this causes all magnetic particles or proteins, including those with attached analyte, to localise close to the Vacutainer™ exit where it is drawn off (Step 3); unwanted sample matrix remains in the Vacutainer™ and is disposed of together with the Vacutainer™; the pre-prepared sample is then ready for transfer into an analysis device (Step 4).

Preferably the one or more reagents each comprise one or more labels for one or more analytes, which label is attached to a magnetic or magnetisable substance, the label comprising:

(a) a recognition moiety for attaching the one or more labels to the one or more analytes; and
(b) a moiety for binding or encapsulating the magnetic or magnetisable substance;

wherein the moiety for binding or encapsulating the magnetic or magnetisable substance comprises a metal-binding protein, polypeptide, or peptide.

PCT/GB07/004,188 (the contents of which are incorporated by reference) discloses the above magnetic recognition labels, which are capable of attaching small quantities of a magnetic (or magnetisable) substance to an analyte via a recognition agent for the analyte. The labels have significant advantages in that they are capable of attaching a very small volume of the magnetic substance to the analyte, so that the analyte can be influenced by magnetic fields, even in a confined space, such as in a microfluidic system.

In this embodiment, by 'attached to' in the present context, it is meant that the attachment is of any type, including specific and non-specific binding and also encapsulation. Thus, the moiety for binding the magnetic or magnetisable substance should be capable of binding or encapsulating (or otherwise attaching in a specific or non-specific manner) the substance in the form of particles or aggregates or the like. These particles or aggregates are much smaller than conventional magnetic beads, typically having less than 100,000 atoms. In accordance with these binding environments, the total volume of the substance bound or encapsulated in a single moiety typically does not exceed $1 \times 10^5$ nm$^3$ (representing a particle or aggregate of the substance having an average of about 58 nm or less). It is thus also preferred in the present invention that the average diameter of the bound particles is 50 nm or less. In this context, average means the sum of the diameters of the number of particles, divided by the number of particles.

Preferably the one or more labels each contain a fusion protein comprising the recognition moiety and the moiety for binding or encapsulating the magnetic or magnetisable substance. In the context of the present invention, a fusion protein is a protein that has been expressed as a single entity recombinant protein using DNA manipulation techniques of molecular biology. Fusion proteins have a number of further advantages. The orientation of the recognition arm of the fusion protein (e.g. the scFv) within the invention will be controlled and therefore more likely to bind its target. Fusion proteins also facilitate the possibility of incorporating a plurality of recognition moieties in a single fusion protein. These recognition sites may be directed against the same target or to different targets. Where two or more recognition moieties are present, the spatial organisation of the recognition moieties on the magnetic substance can be defined and controlled, decreasing problems caused by steric hindrance and random binding to conventional beads. With careful spacing of each recognition moiety within the fusion protein (e.g. by incorporating nucleic acid spacers in the expression system) the tertiary structure of the final protein can be controlled to deploy recognition moieties at spatially selected zones across the protein surface. A further advantage of using fusion proteins is that the number of recognition moieties within each label can be specified and will be identical for every molecule of the label. This contrasts with conventional means of attaching recognition moieties to magnetic beads, where due to the random nature of attachment it is much more difficult to specify the number of recognition moieties and there will be considerable variation in the number that are attached to each magnetic bead.

The moiety for binding the magnetic or magnetisable substance is not especially limited, provided that it is capable of binding the substance and does not interfere with the binding to the analyte. The moiety for binding the magnetic or magnetisable substance comprises a metal-binding protein, polypeptide or peptide (or the metal-binding domain of such a protein polypeptide or peptide). Typically this moiety is capable of binding to, or is bound to, one or more transition and/or lanthanide metal atoms and/or ions, or any compound comprising such ions. Such ions include, but are not limited to, any one or more ions of Fe, Co, Ni, Mn, Cr, Cu, Zn, Cd, Y, Gd, Dy, or Eu.

In the more preferred embodiments of the invention, the one or more metal ions comprise any one or more of $Fe^{2+}$, $Fe^{3+}$, $Co^{2+}$, $Co^{3+}$, $Mn^{2+}$, $Mn^{3+}$, $Mn^{4+}$, $Cd^{2+}$ and $Ni^{2+}$. The most preferred ions for use in the present invention are $Fe^{2+}$ and $Fe^{3+}$ and $Cd^{2+}$, $Co^{3+}$ and $Mn^{2+}$ ions. Typically these ions are bound by lactoferrin, transferrin and ferritin in the case of iron, and metallothionein-2 in the case of cadmium and manganese. The binding of $Fe^{2+}$ is preferably promoted by employing acidic conditions, whilst the binding of $Fe^{3+}$ is preferably promoted by employing neutral or alkaline conditions.

In preferred embodiments of the invention, the metal-binding moiety comprises a protein, or a metal-binding domain of a protein, selected from lactoferrin, transferrin, ferritin (apoferritin), a metallothionein (MT1 or MT2), a ferric ion binding protein (FBP e.g. from *Haemophilus influenzae*), frataxin and siderophores (very small peptides which function to transport iron across bacterial membranes).

The sample collection container according to the present invention may also comprise one or more reagents comprising sets of labels, each label in the set having a different (unique) number of metal-binding moieties. These sets of labels are advantageous because they may allow processing of multiple analytes from one or more samples simultaneously.

The recognition moiety is not especially limited, provided that it is capable of binding selectively to the analyte of interest. Typically, the analytes to which the moiety should bind are selected from a biological molecule (natural or synthetic), an infectious agent or component of an infectious agent (such as a virus or virus particle or virus component), a cell or cellular component, and a small molecule such as an endogenous or exogenous small molecule (e.g. a metabolite, or a pharmaceutical or drug). More specifically, it is preferred that the analytes to which the moiety should bind comprise a virus or virus particle or virus component, a protein, a polypeptide, a glycoprotein, a nucleic acid, such as DNA or RNA, an oligonucleotide, a metabolite, a carbohydrate such as a complex carbohydrate, a lipid, a fat, or a pharmaceutical or drug. These analytes include sugar residues produced by bacteria (e.g. sialic acid) and sugar coats on many bacteria/viruses, as well as altered sugars present in some tumours on their glycoproteins.

The recognition moiety that is capable of binding to the above analytes may itself be any type of substance or molecule, provided that it is suitable for binding to an analyte of interest. Generally, the recognition moiety is selected from an antibody or a fragment of an antibody, a receptor or a fragment of a receptor, a protein, a polypeptide, a peptidomimetic, a nucleic acid, an oligonucleotide and an aptamer. In more preferred embodiments of the invention, the recognition moiety is selected from a variable polypeptide chain of an antibody (Fv), a T-cell receptor or a fragment of a T-cell receptor, avidin, and streptavidin. Most preferably, the recognition moiety is selected from a single chain of a variable portion of an antibody (sc-Fv).

The present invention also provides a method for collecting a sample, which method comprises collecting the sample using a device comprising a sample collection container as defined above, wherein the restraining agent of the one or more bodies are broken down to release the one or more reagents into the sample.

The present invention also provides a method for collecting a sample for a diagnostic purpose, which method comprises collecting the sample using a device comprising a sample collection container as defined above, wherein the restraining agent of the one or more bodies are broken down to release the one or more reagents into the sample.

The present invention also provides a method for processing a sample which has been removed from a human or animal body, which method comprises collecting the sample directly after removal from the human or animal body in a sample collection container as defined above, wherein the restraining agent of the one or more bodies are broken down to release the one or more reagents into the sample.

The present invention also provides a method for assaying a sample, which method comprises collecting the sample in a sample collection container, and thereby reacting the sample with one or more assay reagents contained in the sample collection container to start the assay.

The method is advantageous because it allows direct or immediate incubation of the sample with the assay reagents immediately after sample collection and allows the assay to start whilst the collection container is being transferred to the assay device. Thus the sample can be taken from the sample source, such as a human patient, and directly fed into the sample collection container. The sample may alternatively be fed into the collection container via a suitable extraction device such as a needle and syringe. The method significantly reduces the time to result for assays, in particular in the context of the near patient environment, where the sample is assayed whilst the patient waits and does not therefore need to be stored and sent away for analysis. The method also simplifies and reduces the cost of assays.

The term "start the assay" in the context of the present invention means start the analytical process of the assay excluding the steps of stabilising a sample. The start may include preparing a sample for the analytical process, such as separating components of the sample; and/or purifying, capturing, concentrating, binding, amplifying or isolating a desired analyte; and/or removing of sample components that may interfere with downstream processes. In a preferred embodiment wherein the sample is blood, the start of the assay includes preparation of the sample by separation of blood plasma from other components of the blood. The start of the assay preferably does not include any form of mechanical or physical separation of sample components, such as the use of a gel to form a physical barrier between clotted blood and serum or plasma. The preparation of the sample preferably comprises purifying, capturing, concentrating, binding, amplifying or isolating specific molecular species, such as protein analytes, from the sample and, preferably, does not include separation of larger components, such as cells or blood clots.

Preferably, the start of the assay process does not include the sample preparation, and is any analytical step taking place after the sample preparation. Thus, in this embodiment the start of the assay is the one or more steps wherein one or more reagents react and/or bind and/or interact with any target analytes present in the sample, in order to allow detection, measurement or quantification of the sample or target analytes. For example, the start of the assay may include beginning an enzymatic reaction which results in products for further analysis downstream.

Vacutainers™ are well known in the art to contain one or more additives suitable for such sample preparation steps, such as a clot activator. However, it is not known to include reagents required to start the assay.

The term "assay reagent" means any suitable reagent which is required to start the assay. The one or more assay reagents are preferably independently selected from a protein, a polypeptide, a peptidomimetic, a nucleic acid, an oligonucleotide, an aptamer and organic or inorganic chemical reagents. Preferably the one or more assay reagents are independently selected from an antibody or a fragment of an antibody, a receptor or a fragment of a receptor, an antigen, an enzyme, an enzyme inhibitor, a binding protein, a catalyst and a serum separating agent. In a preferred embodiment, the assay reagent does not include a serum separating agent.

The assay is preferably carried out for a diagnostic purpose. The assay reagents are preferably for enzymatic assays, nucleic acid assays including DNA and RNA assays, protein assays or ALT enzymatic assays. Examples of preferred assay reagents include protease inhibitors, RNase inhibitors, RNase, reverse transcriptase, DNA polymerase, restriction endonucleases, SYBR green, =concanavalin A, antibodies, magnetic antibodies, magnetic microparticles and magnetic nanoparticles such as MACS® beads (Miltenyi Biotech™) guanidine isothiocyanate, glycogen, carrier RNA, sodium chloride, dNTPs, magnesium chloride, and bridging agents such as StemSep®.

In one embodiment the one or more assay reagents are labels for one or more analytes. This embodiment is described in detail above with respect to the sample collection container according to the present invention.

In one embodiment the one or more assay reagents are magnetic or magnetisable and/or are attached to a magnetic or magnetisable substance. This embodiment is described in detail above with respect to the sample collection container according to the present invention.

The sample collection container in this embodiment is preferably a sample collection container as defined above wherein the reagents are assay reagents.

In the methods according to the present invention the sample may be a mammalian sample including a human sample. The sample is typically selected from blood, saliva, urine, amniotic fluid, mucus, ascites fluid, pulmonary liquids (including pleural), lavage (for example pulmonary eastric etc.), biopsy fluid, semen, swabs (for example PAP, oral etc.), sweat, tears, faecal stools, cerebrospinal fluid, wound exudate, synovial fluid and the like.

As described above with respect to the sample collection container according to the present invention, wherein the one or more reagents are magnetic or magnetisable and/or are attached to a magnetic or magnetisable substance the method according to the present invention may further comprises the steps of subjecting the one or more reagents to a magnetic field to influence the one or more reagents. As discussed in detail above, the magnetic field may be used to mix the one or more reagents with the sample and/or to separate, purify and/or isolate the one or more labels, and/or one or more analytes that may be attached to the one or more labels, from one or more further substances in the sample.

The methods according to the present invention may further comprises a step of analysing the one or more labels and/or the one or more analytes to obtain information on one or more analytes that may be attached to the one or more labels. This step of analysing may typically comprise detecting the presence, absence, identity and/or quantity of the one or more labels and/or the one or more analytes.

The step of analysing the one or more labels and/or the one or more analytes may be carried out using a fluidic device including a microfluidic device or a nanofluidic device.

The present invention also provides the use of a sample collection container as defined above for collecting a sample from a human or animal body. The sample may have already been removed from the human or animal body by an appropriate device such as a needle, and is then directly collected into the sample collection container according to the present invention. The present invention also provides the use of a sample collection container as defined above for processing a sample.

A second aspect of the present invention concerns a cartridge system for use in detecting one or more analytes in a sample, especially a biological sample wherein reagents within the cartridge system are stored within bodies as described above in respect of the sample collection container according to the present invention.

A cartridge system is disclosed in PCT/GB2007/003666 (the contents of which are incorporated by reference), wherein the reagent component stores the reagents. The cartridge system has many advantages including that waste products from the assay may be neatly washed into a compartment, reservoir or void situated in the reagent component itself. This removes the need for the user to contact any waste products and conveniently seals them from the surroundings. This may be particularly important if any of the assay reagents are toxic, or if the sample under investigation is potentially infectious, or dangerous in any way. The system has the further advantage that the user does not need to handle or prepare any reagents, since they are stored in the reagent component.

Despite the clear advantages of the cartridge system disclosed in PCT/GB2007/003666, there is an ongoing requirement to provide an improved cartridge system having a longer shelf life and less stringent storage conditions placed upon it.

It is an aim of the present invention to solve the above problems and improve on known cartridge systems, such as those outlined above.

Accordingly, in a second aspect the present invention provides a cartridge system comprising:
(a) a reagent component for storing one or more reagents; and
(b) a processing component for processing the one or more reagents in an assay;
wherein one or more of the components comprise one or more reagent bodies, wherein each body comprises one or more reagents confined by a restraining agent, wherein the restraining agent is capable of being broken down to release the one or more reagents, and wherein the reagent component and the processing component are configured to be coupled together to form a cartridge, and wherein the reagent component and/or the processing component comprise at least one compartment configured to accept waste from the assay, the reagent component not taking part in processing the reagents in the assay, except to accept waste from the processing component.

One or more of the components may comprise the bodies. Accordingly, in one embodiment the reagent component and/or the processing component comprise the bodies. In a preferred embodiment, the reagent component comprises the bodies.

The reagents are provided in the bodies, as described above in the collection container aspect of the present invention. In one embodiment the reagents are present in the core of bodies encapsulated by an outer shell comprising the restraining agent, as described above. In another embodiment, the reagents are confined in a mixture with the restraining agent, as described above. The reagents may be stabilized by restraining agent in the outer shell or mixture whilst the cartridge is stored ready for use. When the cartridge system is ready for use or in use the restraining agent of the bodies may be broken down chemically, as described above for the bodies in the sample collection device according to the first aspect of present invention. For example the restraining agent of the bodies may be dissolved by a fluid. The fluid may be a reaction medium in the cartridge system which is stored separately to the bodies during storage. When the cartridge system is ready for use, or in use, the bodies may be contacted with the fluid to release the one or more reagents. Accordingly, the cartridge system may configured such that coupling the reagent component to the processing component causes a fluid to pass into the reagent component and the one or more reagents are released from the bodies and enter the processing component from the reagent component. In one embodiment, the fluid may be a sample for analysis.

The cartridge system has a longer shelf life when the reagents are contained within the bodies because the restraining agent of the bodies may act as a barrier to the surrounding environment and stabilize the reagents. This may be particularly advantageous for reagents which previously required storage at low temperatures or had a short shelf life.

The restraining agent of each body and the one or more reagents in the cartridge system of the second aspect of the present invention are the same as the body and reagents as defined above in respect of the sample collection device according to the present invention.

As discussed above, in one embodiment wherein the one or more reagents are confined by an outer shell, the outer shell may be broken down to release the one or more reagents at a given pH, after a certain length of time and/or when contacted with a specific solution. This is particularly advantageous for reagents which are liquid unstable, and therefore unsuitable for pre-mixing. This embodiment is particularly advantageous when used in the cartridge system because the bodies can be easily introduced into the cartridge system, which is especially advantageous in a microfluidic device. Less complicated microfluidics are needed in the cartridge if the reagents can be introduced through the use of bodies rather than input ports. Further, the exact quantities of reagents can be added to the cartridge device relatively easily.

As discussed above for the sample collection container, the cartridge system may comprise two or more different types of reagent bodies in one or more different components, wherein the restraining agents differ in order to allow release of different reagents at different time periods and/or different pHs and/or when contacted with different solutions. As shown in FIG. 4, the outer shells of the bodies, referred to as capsules in the figure, may be contained in a sample collection container, wherein some outer shells are dissolved to release the reagents. The sample and the bodies may then be introduced into a microfluidic cartridge device, wherein the outer shells of other bodies dissolve at different times or locations to release the reagents as required.

The cartridge system is also advantageous in that the same processing component design may be employed for several different assays, simply by using different reagent components. Each reagent component may comprise different reagent bodies, as described above in the first aspect of the present invention.

The structure of the cartridge system is defined in PCT/GB2007/003666, the contents of which are incorporated by reference. The components of the cartridge system are described below.

FIGS. 5, 6a and 6b and 7 show example structures of the cartridge system.

Figure 5:
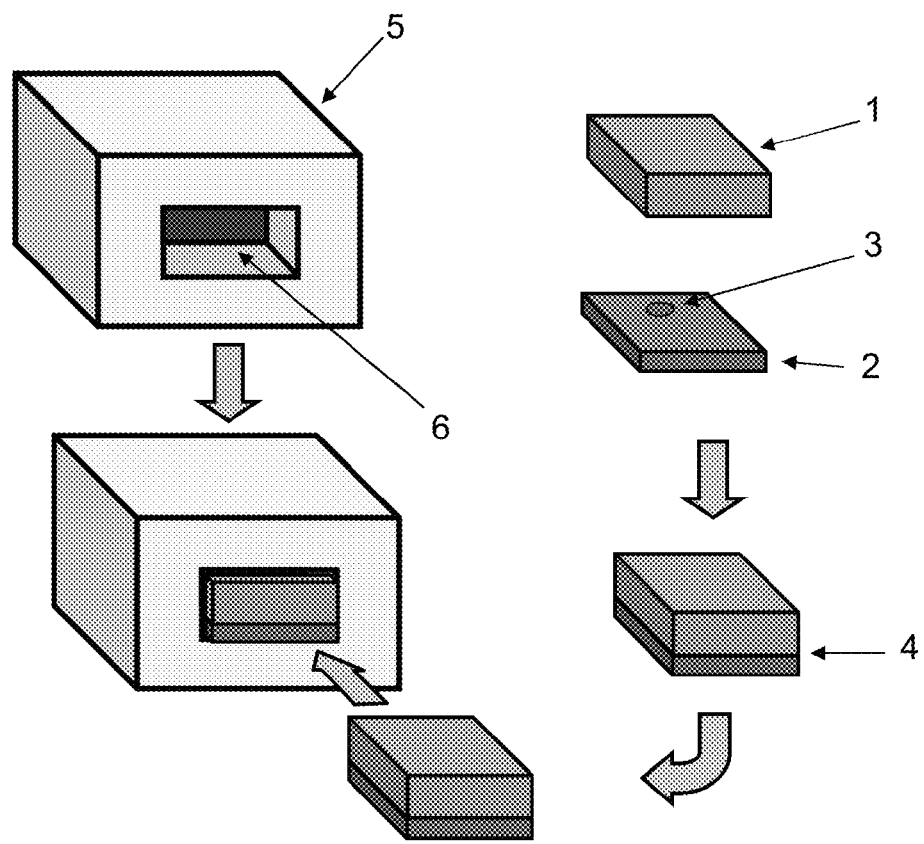

FIG. 5 illustrates the principle parts of the cartridge system—1 is a reagent storage component capable of storing multiple types of reagent in a variety of different volumes, 2 is a reagent processing component incorporating microfluidic channels, reaction zones and valving elements, 3 is a cavity for receiving a test sample, 4 is the complete processing cartridge which results from 1 and 2 being coupled together, 5 is the processing instrument which receives the cartridge through slot 6—the instrument 5 enables operation of various liquid transport, valving and detection means.

Figure 6A:
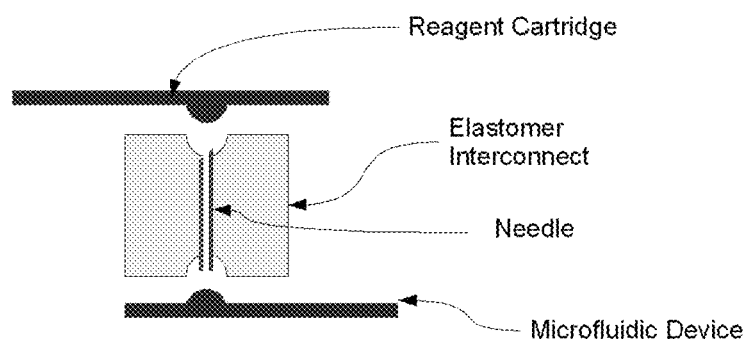
Figure 6B:
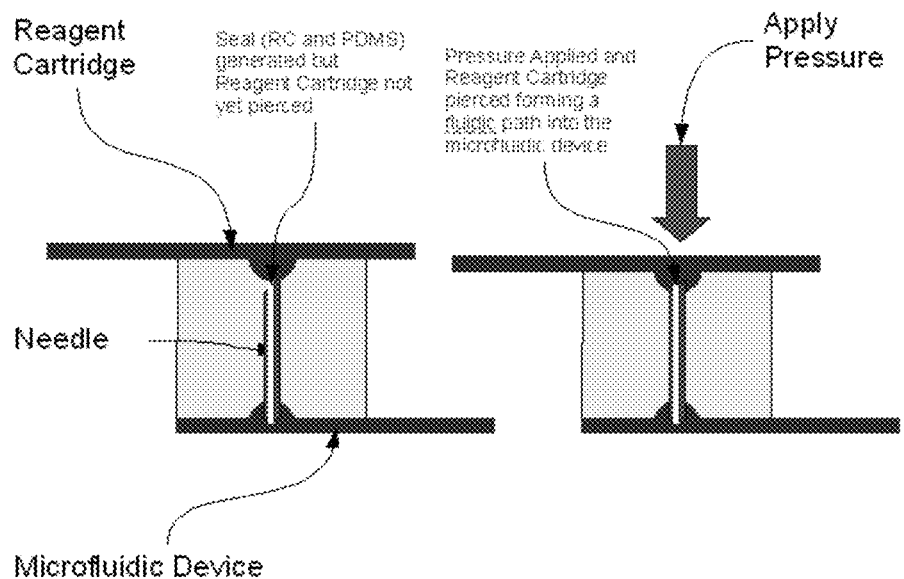

FIGS. 6a and 6b show an exemplary cartridge interconnect system.

Figure 7:
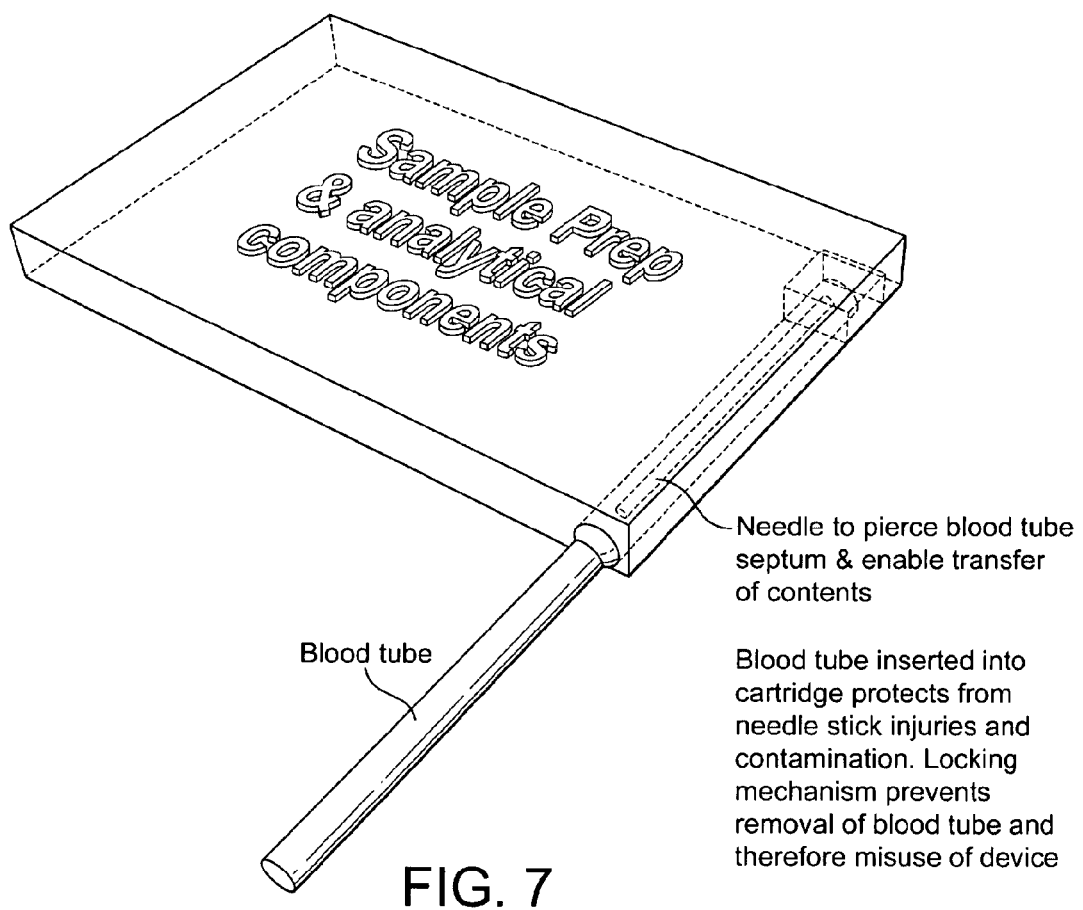

FIG. 7 shows a sample zone at the edge of a cartridge system. This sample zone is configured to accept a blood tube (i.e. the sample is a whole blood sample). It is advantageous since the needle for piercing the blood tube is hidden within the sample zone to protect the user from needle stick injuries, and contamination.

The cartridge system typically comprises a sensing element for detecting an analyte (although in some embodiments the sensing element may be part of an assay device into which the cartridge is inserted and thus need not be present in the cartridge itself, or may be present in a third component (sensing component) of the system). The location of the sensing element or component is not especially limited, and may be selected depending upon the particular assay in question. Thus the sensing element or component may be part of the reagent component or the processing component. In a preferred embodiment the reagent component comprises the sensing element or component.

Thus in one embodiment the cartridge system comprises:
(a) a reagent component for storing one or more reagents, wherein the reagent component comprises one or more reagent bodies, wherein each body comprises one or more reagents confined by a restraining agent, wherein the restraining agent is capable of being broken down to release the one or more reagents;
(b) a processing component for processing one or more reagents in an assay; and
(c) a sensing component comprising at least one sensing element for detecting an analyte;

wherein one or more of the components comprise one or more reagent bodies, wherein each body comprises one or more reagents confined by a restraining agent, wherein the restraining agent is capable of being broken down to release the one or more reagents, wherein the reagent component, the processing component and the sensing component are separate components configured to be coupled together to form a cartridge.

In this embodiment the one or more or all of reagent component, the processing component and the sensing component comprise the reagent bodies. In a preferred embodiment, the reagent component comprises the reagent bodies.

In this embodiment, the sensor component is typically a separate third component of the cartridge, e.g. in a point-of-use kit. The sensor substrate can advantageously be prefabricated as a separate component prior to assembly in the reagent cartridge.

It is preferred that the sensing component is configured to be coupled, optionally removably coupled, to either the reagent component or the processing component prior to coupling of the reagent and processing components. Typically, the sensing component and the reagent or processing component are provided pre-coupled to each other. In this context pre-coupled means that the sensing component and the reagent or processing component are separate components that are coupled together (optionally removably so) during manufacture, and are provided to the user (as part of a system or kit) in a coupled form along with a separate component (the other of the reagent or processing component that the sensor component is not coupled to). In all of these embodiments it is preferred that the reagent component comprises at least one compartment configured to accept waste from the processing component.

In a further embodiment, the invention provides a cartridge system comprising:
(a) a reagent component for storing one or more reagents, wherein the reagent component comprises one or more reagent bodies, wherein each body comprises one or more reagents confined by a restraining agent, wherein the restraining agent is capable of being broken down to release the one or more reagents;
(b) a processing component for processing one or more reagents in an assay; and
(c) a sample preparation component for preparing a sample for the assay;

wherein the reagent component and the processing component are configured to be coupled together to form a cartridge.

In this embodiment the one or more or all of reagent component, the processing component and the sample preparation component comprise the reagent bodies. In a preferred embodiment, the reagent component and/or the sample preparation component comprises the reagent bodies.

In this embodiment, the system comprises a further component, a sample preparation component, which prepares the sample for the assay before delivering the prepared sample to the processing component. This embodiment offers many advantages. For example, different samples will require different types of preparation (e.g. a urine sample will be different from a blood sample) and the sample preparation component may allow such different samples to be used on the same processing component by pre-processing the sample before it is delivered to the processing component for carrying out the assay.

In all embodiments of the invention, it is also advantageous in that the cartridge can provide for simultaneous multi-analyte detection. A particularly advantageous means of achieving this is to configure the reaction chamber within which sensing takes place such that multiple methods of sensing can be employed, for example, both electro-chemical means and optical means.

In the context of the present invention all of the cartridge systems described may be in the form of a kit, for assembly and/or coupling at the point of use by a user.

The type of sensing element for detecting an analyte is not especially limited. It may be selected depending on the assay method and/or analyte in question. Typically the element comprises one or more of a biosensor array, an electrochemical biosensor element, and an optical biosensor element.

In the present invention it is preferred that the reagent component and/or the processing component and/or the sensing component comprises one or more connection ports for establishing one or more connections with the other component(s), on coupling the components together.

In a further preferred embodiment, the cartridge system is configured such that coupling the reagent component to the processing component causes one or more reagents to enter the processing component from the reagent component. The reagents are released from the reagent bodies by means of break down of the restraining agent. Coupling may be employed to initiate a "priming" cycle, e.g. by flooding the device with appropriate liquids, such as a buffer solution. This liquid may act to dissolve the restraining agent of the bodies, thus releasing the reagents.

The cartridge system of the present invention will typically be employed in a biological assay. In such assays, it is the norm to test a sample from a patient in order to establish a diagnosis (sometimes in combination with a preferred treatment—termed theranostics). Thus, in most embodiments the reagent component and/or the processing component and/or the sample preparation component comprises a sample zone, configured to accept a sample. It is particularly preferred that the sample zone is configured to accept a sample collection container as defined in the first aspect of the present invention.

The location of the sample zone is not especially limited, provided that it is suitable for the particular assay in question. Sometimes the sample zone is not present in the cartridge system at all, but is instead in the assay device. However, preferably the sample zone is in the processing component (and more preferably in the sample preparation component when present).

In preferred embodiments, the sample zone is configured to deliver the sample to the processing component. In this embodiment the sample may act to dissolve the restraining agent of the bodies thus releasing the reagents.

The sample will be assayed with a view to detecting the identity and/or quantity of a particular analyte which may be in the sample. The type of analyte is not especially limited, and the cartridge system of the invention may be adapted to many types of analyte, including assays for multiple analytes, sequentially or simultaneously. Typically, the analyte is selected from a biological molecule, a virus or virus component, and a cell or a cell component. Examples of analytes include whole cells such as liver cells, enzymes, whole viruses (e.g. Hepatitis C virus (HCV) and Human Immunodeficiency Virus (HIV)), proteins polypeptides and peptides, and nucleic acids such as DNA and/or RNA. Also included are carbohydrates and small molecules, such as drugs, pharmaceuticals and metabolites.

Typically the reagent component comprises a plurality of reagent storage zones. These may comprise one or more reagents suitable for carrying out one or more processing steps selected from analyte and/or sample preparation, analyte and/or sample separation, analyte and/or sample concentration, analyte and/or sample amplification, analyte and/or sample purification, analyte and/or sample labelling, and analyte and/or sample detection. Any one or more or all of the reagent storage zones may comprise the reagent bodies comprising one or more reagents.

When the sample preparation component is present, it may comprise one or more of the following areas or zones: a sample preparation zone, a sample separation zone, a sample concentration zone, a sample amplification zone, a sample purification zone, a sample labelling zone, and/or a sample quality control zone. Any one or more or all of the sample preparation zones may comprise the reagent bodies comprising one or more reagents.

The sample preparation component may be formed of a single component that may be configured to attach to either or both of the reagent storage component and the processing component. This single component may be pre-coupled to either of the other components, or may be coupled to them by the user, either by hand or by use of an assay device. In some embodiments, the sample processing component comprises two sub-components: a sample preparation reagent component comprising one or more reagent bodies, wherein each body comprises one or more reagents confined by a restraining agent, wherein the restraining agent is capable of being broken down to release the one or more reagents, and a sample preparation processing component. These components may function in a similar way to the two components of the main cartridge—the reagent component providing the reagents necessary for sample preparation whilst the processing component uses these reagents in conjunction with the sample itself to prepare the sample for introduction into the processing component of the main cartridge to perform the assay. The sub-components may be pre-coupled or may be configured to be coupled together by the user.

The analyte/sample may be delivered attached to magnetic (or other) beads as may one or more reagents from the reagent component. Accordingly, the one or more reagents from the reagent component may be magnetic or magnetisable and/or may be attached to a magnetic or magnetisable substance, as described above in detail in the first embodiment of the present invention.

If magnetic beads are employed, the connection means for coupling the components together, and any appropriate conduits in the components are appropriately configured to allow beads to move to and from the required zones in the components.

When the one or more reagents are magnetic or attached to a magnetic substance, the processing component and/or the sample preparation component comprise means to apply a magnetic field to influence the reagents. For example, the magnetic field may be used to mix the reagents and the sample and/or to separate, purify and/or isolate the one or more labels, and/or one or more analytes that may be attached to the one or more labels, from one or more further substances in the sample.

The cartridge system according to the present invention is preferably a microfluidic or nanofluidic device.

Preferably, the processing component is a microfluidic component, since this allows assays to be carried out speedily on a small quantity of sample, which is ideal in the near-patient environment. However, in some instances larger macro layouts may be preferred.

Whether the processing is microfluidic or not, there are four types of particularly preferred assay:
1. Nucleic acid assays (such as DNA or RNA).
2. Enzymatic assays (an ALT (Alanine Aminotransferase, a liver enzyme) are especially preferred in the context of hepatitis infection).
3. Protein assays (typically using antibodies for detection, e.g. on a microarray—preferred analytes of interest include hepatitis (A, B and/or C) and interferons alpha (IFN-α) and gamma (IFN-γ).
4. Small molecule assays (such as pharmaceuticals or drugs—typical methods involve competition assays using antibodies). Therapeutic drug monitoring (TDM) is also an option.

The present invention also provides an assay method for one or more analytes in a sample, which method comprises:
(a) introducing the sample into a sample zone of a reagent component and/or the sample zone of a processing component and/or the sample zone of a sample preparation component, in a cartridge system as defined above;
(b) coupling the cartridge system to an assay device configured to accept the cartridge; and
(c) assaying for the one or more analytes using the assay device.

In this method the sample is typically a mammalian sample such as a human sample. The sample may be selected from blood, saliva, urine, amniotic fluid, mucus, ascites fluid, pulmonary liquids (including pleural), lavage (for example pulmonary eastric etc.), biopsy fluid, semen, swabs (for example PAP, oral etc.), sweat, tears, faecal stools, cerebrospinal fluid, wound exudate, synovial fluid and the like.

In one embodiment wherein the cartridge system is configured to accept a sample collection container as defined in the first aspect of the present invention and the one or more reagents in the sample collection container are magnetic and/or are attached to a magnetic substance, the method further comprises a step of subjecting the one or more reagents in the sample collection container to a magnetic field in the sample zone to influence the one or more reagents. This step is the same as the method described above in the first aspect of the present invention. The magnetic field is employed preferably to mix the one or more reagents with the sample and/or to separate, purify and/or isolate the one or more labels, and/or one or more analytes that may be attached to the one or more labels, from one or more further substances in the sample.

The present invention also provides a reagent component for storing one or more reagents, which reagent component is configured to be coupled together with a processing component and optionally with a sensing component and further optionally with a sample preparation component to form a cartridge, wherein the reagent component comprises at least one compartment configured to accept waste from the processing component, and wherein the reagent component is not configured to take part in processing the reagents in the assay, except to accept waste from the processing component, wherein the reagent component comprises one or more reagent bodies, wherein each body comprises one or more reagents confined by a restraining agent, wherein the restraining agent is capable of being broken down to release the one or more reagents. The reagent bodies are the same as the reagent bodies described above in the first aspect of the present invention.

The present invention also provides the use of a cartridge system, cartridge and/or reagent component as defined above in an assay method for identifying an analyte in a sample.

The invention will now be described by way of example only with reference to the following specific embodiments.

EXAMPLES

Buffer for Reagents at pH 7.4
Materials and Reagents:
25 mM Tris (hydroxymethyl)methylamine
Sucrose
Sodium azide
Bovine serum albumin (BSA)
2M hydrochloric acid
0.2 µm filter
Procedure:
To 400 ml 25 mM Tris (hydroxymethyl)methylamine, add 150 g sucrose, 1g BSA and 0.4 g sodium azide. Adjust pH to 7.4. Adjust volume to 500 ml. Filet through a 2 µm filter. Store at 2-8° C. until required.

Buffer for Reagents at pH 8.5
Materials and Reagents:
Sodium tetraborate buffer (9.5g sodium tetraborate decahydrate in 500 ml water)
Sucrose
Sodium azide
Bovine serum albumin (BSA)
2M hydrochloric acid
0.2 µm filter
Procedure:
To 400 ml sodium tetraborate buffer, add 150 g sucrose, 1 g BSA and 0.25 g sodium azide. Adjust pH to 8.5. Adjust volume to 500 ml. Filet through a 2 µm filter. Store at 2-8° C. until required.

Buffer for Reagents at pH 8.0
Materials and Reagents:
25 mM ammonium bicarbonate
Sucrose
Sodium azide
Bovine serum albumin (BSA)
2M hydrochloric acid
0.2 µm filter
Procedure:
To 400 ml ammonium bicarbonate buffer, add 75 g sucrose, 1 g BSA and 0.4 g sodium azide. Adjust pH to 8.0. Adjust volume to 500 ml. Filet through a 2 µm filter. Store at 2-8° C. until required.

The reagent of interest is mixed in with the most appropriate carbohydrate buffer or directly re-suspended or dissolved in the carbohydrate buffer. The equipment used to freeze the reagents (e.g. a rotating drum) is cooled to the necessary temperatures (e.g. −60° C. or less) and small volumes (typically 15 µl) dispensed onto the drum to freeze into reagent bodies (pearls). The reagent bodies (pearls) are dispensed into vials for freeze drying.

The invention claimed is:

1. A sample collection container comprising first and second reagent bodies, wherein the first reagent body comprises one or more first reagents confined by a first restraining agent and dispersed therethrough, the second reagent body comprising one or more second reagents confined by a second restraining agent and dispersed therethrough, said second restraining agent being different from the first restraining agent, wherein the first restraining agent is capable of being broken down to release the one or more first reagents and the second restraining agent is capable of being broken down to release the one or more second reagent.

2. A sample collection container according to claim 1, wherein the one or more first reagents are confined by an outer shell, wherein the outer shell comprises the restraining agent.

3. A sample collection container according to claim 1, wherein the first or second restraining agent is capable of being broken down at a desired pH.

4. As sample container according to claim 2, wherein the thickness of the outer shell is set to a thickness which allows the one or more first reagents to be released after a desired time period.

5. A sample collection container according to claim 1, wherein the first or second restraining agent comprises light-sensitive bonds and wherein light is capable of disrupting the light-sensitive bonds thereby breaking down said first or second restraining agent.

6. A sample collection container according to claim 1, wherein the first or second restraining agent is capable of being broken down when contacted with a fluid and wherein the fluid breaks down said restraining agent by dissolving said restraining agent, enzymatic degradation of said restraining agent or bacterial decomposition of said restraining agent.

7. A sample collection container according to claim 1, wherein the first or second restraining agent comprises a desiccated or lyophilized substance.

8. A sample collection container according to claim 1, wherein the first or second restraining agent comprises one or more carbohydrates.

9. A sample collection container according to claim 8, wherein the one or more carbohydrates are selected from sucrose and trehalose.

10. A sample collection container according to claim 1, wherein the first or second restraining agent comprises one or more polymers.

11. A sample collection container according to claim 10, wherein the polymers are selected from derivatives of acrylic acid and cellulose.

12. A sample collection container according to claim 1, wherein the sample collection container comprises two or more first reagents, wherein the two or more first reagents are encapsulated together in the one or more first reagent body.

13. A sample collection container according to claim 1, wherein the one or more first reagents are different from the one or more second reagents.

14. A sample collection container according to claim 1, wherein the sample collection container is suitable for collection of samples selected from blood, saliva and urine.

15. A sample collection container according to claim 14, wherein the sample collection container is a rubber-capped vacuum tube.

16. A sample collection container according to claim 1, wherein the one or more first reagents are independently selected from a protein, a polypeptide, a peptidomimetic, a nucleic acid, an oligonucleotide, an aptamer and organic or inorganic chemical reagents.

17. A sample collection container according to claim 16, wherein the one or more first reagents are independently selected from an antibody or a fragment of an antibody, a receptor or a fragment of a receptor, an antigen, an enzyme, an enzyme inhibitor, a binding protein, a catalyst, a serum separating agent, a blood clotting activator, an anticoagulant, a detergent and a salt.

18. A sample collection container according to claim 1, which further comprises one or more non-confined reagents.

19. A sample collection container according to claim 18, wherein the one or more non-confined reagents are selected from a blood clotting activator, an anticoagulant, a detergent and a salt.

20. A sample collection container according to claim 1, wherein one or more of the one or more first reagents are labels for one or more analytes.

21. A sample collection container according to claim 1, wherein the one or more first reagents are magnetic or magnetisable and/or are each attached to a magnetic or magnetisable substance.

22. A sample collection container according to claim 21, wherein the one or more first reagents are magnetic beads and/or the magnetic or magnetisable substance is a magnetic bead.

23. A sample collection container according to claim 22, wherein each of the one or more first reagents comprises a label for an analyte, which label is attached to the magnetic or magnetisable substance, the label comprising:
    (a) a recognition moiety for attaching the one or more labels to the one or more analytes; and
    (b) a moiety for binding or encapsulating the magnetic or magnetisable substance;
    wherein the moiety for binding or encapsulating the magnetic or magnetisable substance comprises a metal-binding protein, polypeptide, or peptide.

24. A sample collection container according to claim 23, wherein the one or more labels each contain a fusion protein comprising the recognition moiety and the moiety for binding or encapsulating the magnetic or magnetisable substance.

25. A sample collection container according to claim 23, wherein the moiety for binding or encapsulating the magnetic or magnetisable substance comprises a protein, or a metal-binding domain of a protein, selected from lactoferrin, transferrin, ferritin, a ferric binding protein, frataxin, a siderophone and a MT.

26. A sample collection container according to claim 20, wherein the analyte comprises a virus or virus particle or virus component, a protein, a polypeptide, a glycoprotein, a nucleic acid, such as DNA or RNA, an oligonucleotide, a metabolite, a carbohydrate such as a complex carbohydrate, a lipd, a fat, or an endogeneous or exogeneous small molecule such as a pharmaceutical or drug.

27. A method for assaying a sample, which method comprises collecting a sample in a sample collection container of claim 1, and thereby reacting the sample with one or more assay reagents contained in the sample collection container to start the assay.

28. A method according to claim 27, wherein the sample is a mammalian sample.

29. A method according to claim 28, wherein the sample is a human sample.

30. A method according to claim 27, wherein the sample is selected from blood, saliva and urine.

31. A method according to claim 27, wherein the method further comprises the steps of subjecting the one or more reagents to a magnetic field to influence the one or more reagents.

32. A method according to claim 31, wherein the magnetic field is employed to mix the one or more reagents with the sample.

33. A method according to claim 31, wherein the one or more reagents are labels for one or more analytes and the magnetic field is employed to separate, purify and/or isolate the one or more labels, and/or one or more analytes that may be attached to the one or more labels, from one or more further substances in the sample.

34. A method according to claim 33, which method further comprises a step of analysing the one or more labels and/or the one or more analytes to obtain information on one or more analytes that may be attached to the one or more labels.

35. A method according to claim 34, in which analysing the one or more labels and/or the one or more analytes comprises detecting the presence, absence, identity and/or quantity of the one or more labels and/or the one or more analytes.

36. A method according to claim 27, which method is carried out using a fluidic device.

37. A method according to claim 36, wherein the fluidic device is a microfluidic device or a nanofluidic device.

38. A sample collection container according to claim 1, wherein the first restraining agent is capable of being broken down to release the one or more first reagents within a first time period, and wherein the second restraining agent is capable of being broken down to release the one or more second reagents within a second time period, the second time period being different from the first time period.

39. A sample collection container according to claim 1, wherein the first restraining agent is capable of being broken down to release the one or more first reagents at a first pH, and wherein the second restraining agent is capable of being broken down to release the one or more second reagents at a second pH, the second pH being different from the first pH.

40. A sample collection container according to claim 1, wherein the first restraining agent is capable of being broken down to release the one or more first reagents by contact with a first fluid or solution, and wherein the second restraining agent is capable of being broken down to release the one or more second reagents by contact with a second fluid or solution, the second fluid or solution being different from the first fluid or solution.

41. A sample collection container according to claim 1, wherein one of the reagents is released during a downstream analysis step.

42. A sample collection container according to claim 41, wherein one of the reagents is released in a microfluidic device.

\* \* \* \* \*